(12) United States Patent　　(10) Patent No.: US 7,144,153 B2
Sato　　(45) Date of Patent: Dec. 5, 2006

(54) MEASURING APPARATUS

(75) Inventor: Shu Sato, Kanagawa-ken (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 42 days.

(21) Appl. No.: 10/929,570

(22) Filed: Aug. 31, 2004

(65) Prior Publication Data

US 2005/0046853 A1　　Mar. 3, 2005

(30) Foreign Application Priority Data

Sep. 2, 2003　　(JP)　　............................. 2003-310059

(51) Int. Cl.
*G01K 13/00* (2006.01)
*G01N 21/55* (2006.01)

(52) U.S. Cl. ........................ 374/142; 356/445; 374/141

(58) Field of Classification Search ................ 374/141, 374/142; 356/445
See application file for complete search history.

(56) References Cited

U.S. PATENT DOCUMENTS

| 4,099,921 | A | 7/1978 | Allington | |
|---|---|---|---|---|
| 6,654,123 | B1* | 11/2003 | Shimizu | ..................... 356/445 |
| 6,791,691 | B1* | 9/2004 | Ohtsuka et al. | ............. 356/445 |
| 6,885,454 | B1* | 4/2005 | Naya et al. | ................. 356/445 |
| 6,970,256 | B1* | 11/2005 | Jackson | ....................... 356/630 |
| 2001/0040680 | A1 | 11/2001 | Kubo et al. | |
| 2002/0145737 | A1* | 10/2002 | Kubo et al. | ................. 356/445 |
| 2003/0189707 | A1* | 10/2003 | Naya et al. | ................. 356/445 |
| 2005/0030543 | A1* | 2/2005 | Ohtsuka et al. | ............. 356/445 |
| 2005/0046854 | A1* | 3/2005 | Kunuki et al. | .............. 356/445 |

FOREIGN PATENT DOCUMENTS

| EP | 1 186 881 A1 | 3/2002 |
|---|---|---|
| EP | 1 243 916 A2 | 9/2002 |
| JP | 6-167443 A | 6/1994 |

OTHER PUBLICATIONS

"Surface Refractor-Sensor using Evanescent Waves: Principles and Instrumentations" by Takayuki Okamoto (Spectrum Researches, vol. 47, No. 1 (1998), pp. 21 to 23 & pp. 26 and 27).
"Porous Gold in Surface Plasmon Resonance Measurement" by D.V. Noort, K. Johansen, and C.F. Mandenius (EUROSENSORS XIII, 1999, pp. 585-588).
"Surface Plasmon Resonance Interferometry for Micro-Array Biosensing" by P.I. Nikitin, A.N. Grigorenko, A.A. Beloglazov, M.V. Valeiko, A.I. Savchuk, and O.A. Savchuk (EUROSENSORS XIII, 1999, pp. 235-238).

* cited by examiner

*Primary Examiner*—Diego Gutierrez
*Assistant Examiner*—Megann E Vaughn
(74) *Attorney, Agent, or Firm*—Sughrue Mion, PLLC

(57) ABSTRACT

In a surface plasmon resonance sensor, a sensor unit includes a dielectric block, a thin film layer which is formed on the upper surface of the dielectric block, and a sample holding portion. An incubator is provided, the surface plasmon resonance sensor is spatially isolated from the surroundings by placing it in the measuring system, the temperature of the measuring system is measured and temperature change of the sensor unit after it is conveyed to the measuring system from the incubator is estimated on the basis of the temperature difference between the temperature of the incubator and the temperature of the measuring system, and the sensor unit is conveyed to the measuring system to perform the measurement within a time for which the temperature of the sensor unit does not unacceptably change.

2 Claims, 11 Drawing Sheets

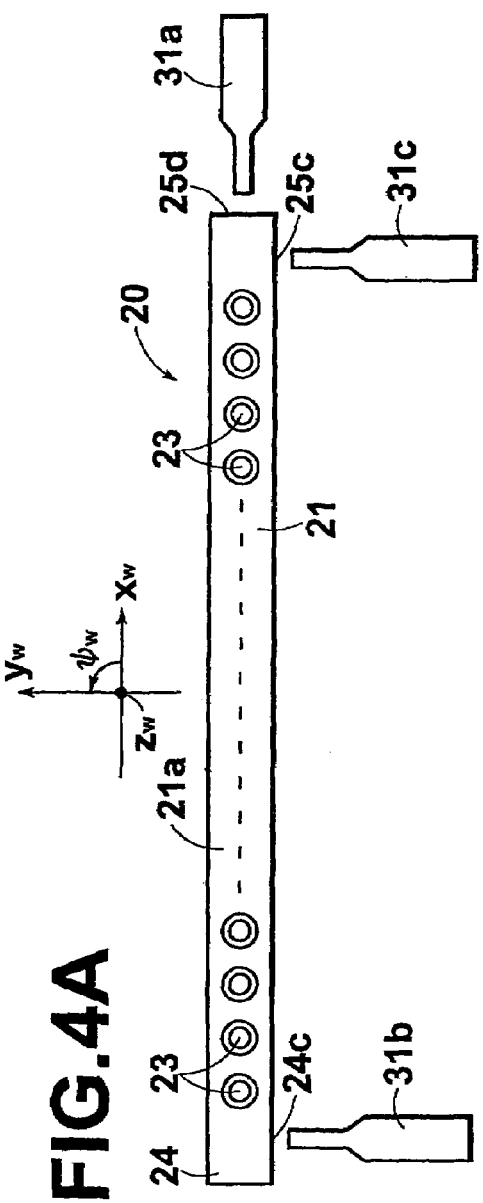
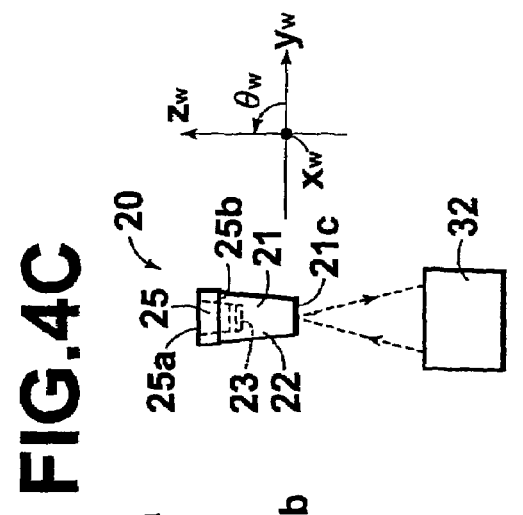
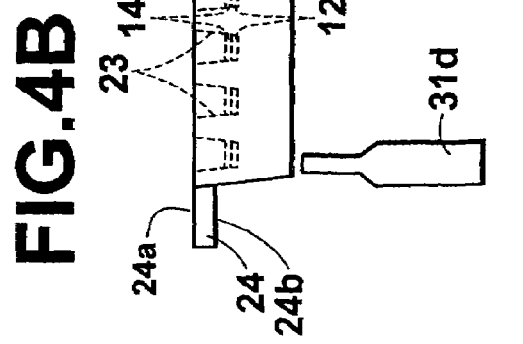

TEMPERATURE DIFFERENCE VS THERMAL TIME CONSTANT

E48R DISSIPATED TEMPERATURE BY NATURAL CONVECTION (THE ENTIRE WELL)

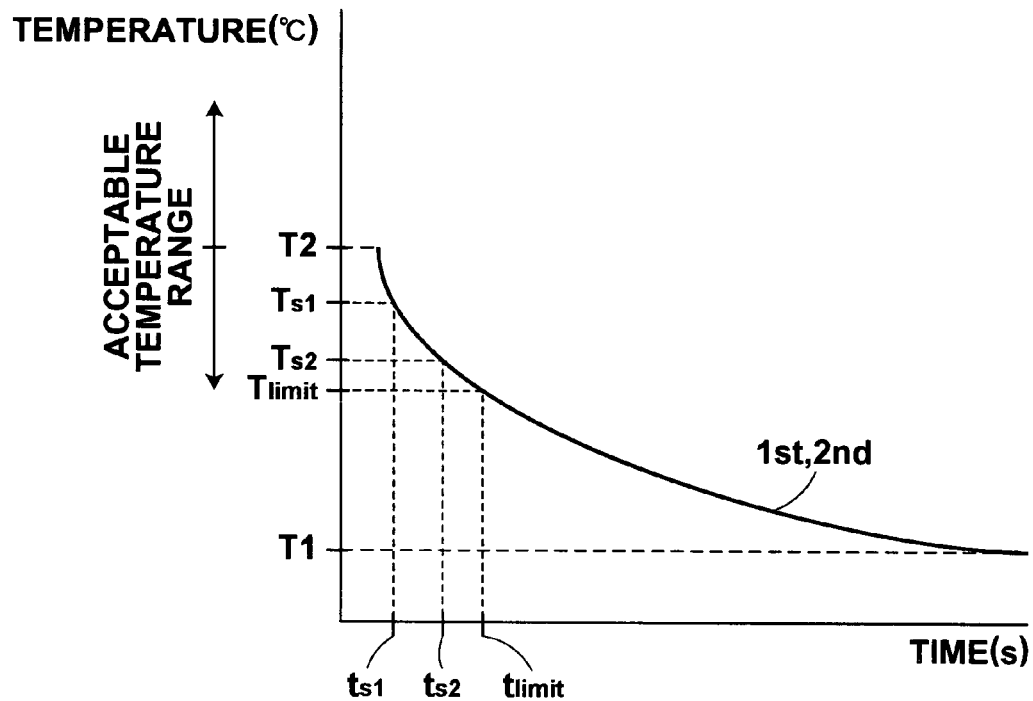
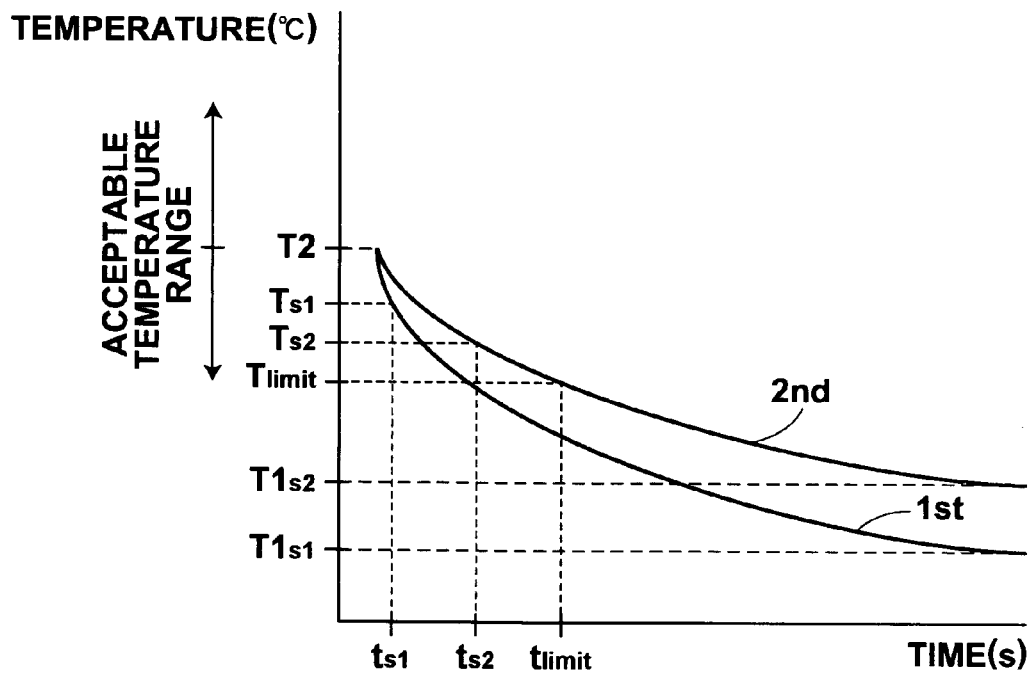

MEASURING APPARATUS

BACKGROUND OF THE INVENTION

1. Field of the Invention

This invention relates to a measuring apparatus such as a surface plasmon resonance sensor for analyzing a material in a sample on the basis of generation of surface plasmon.

2. Description of the Related Art

In metal, free electrons vibrate in a group to generate compression waves called plasma waves. The compression waves generated in a metal surface are quantized as surface plasmon.

There have been proposed various surface plasmon resonance sensors for quantitatively analyzing a material in a sample utilizing a phenomenon that such surface plasmon is excited by light waves. Among those, one employing a system called "Kretschmann configuration" is best known. See, for instance, Japanese Unexamined Patent Publication No. 6(1994)-167443.

The surface plasmon resonance sensor using the Kretschmann configuration basically comprises a dielectric block shaped, for instance, like a prism, a metal film which is formed on one face of the dielectric block and is brought into contact with a sample, a light source emitting a light beam, an optical system which causes the light beam to enter the dielectric block so that total internal reflection conditions are satisfied at the interface of the dielectric block and the metal film and various angles of incidence of the light beam to the interface including an angle of incidence at which attenuation in total internal reflection is generated due to surface plasmon resonance (the attenuation angle) can be obtained, and an information obtaining means which detects the intensity of the light beam reflected in total internal reflection at the interface and obtains information on the attenuation angle or the change thereof.

In order to obtain various angles of incidence of the light beam to the interface, a relatively thin incident light beam may be caused to impinge upon the interface changing the angle of incidence or a relatively thick incident light beam may be caused to impinge upon the interface in the form of convergent light or divergent light so that the incident light beam includes components impinging upon the interface at various angles. In the former case, the light beam which is reflected from the interface at an angle which varies as the angle of incidence changes may be detected by a photodetector which is moved in synchronization with the change of the angle of incidence or by an area sensor extending in the direction in which reflected light beam is moved as the angle of incidence changes. In the latter case, an area sensor which extends in directions in which it can detect all the components of light reflected from the interface at various angles may be used.

In such a surface plasmon resonance sensor, when a light beam impinges upon the metal film at a particular angle of incidence $\theta sp$ not smaller than the angle of total internal reflection, evanescent waves having an electric field distribution in the sample in contact with the metal film are generated and surface plasmon is excited in the interface between the metal film and the sample by the evanescent waves. When the wave vector of the evanescent light is equal to the wave number of the surface plasmon and wave number matching is established, the evanescent waves and the surface plasmon resonate and light energy is transferred to the surface plasmon, whereby the intensity of light reflected in total internal reflection at the interface of the dielectric block and the metal film sharply drops. The sharp intensity drop is generally detected as a dark line by the photodetector.

The aforesaid resonance occurs only when the incident light beam is p-polarized. Accordingly, it is necessary to set the surface plasmon sensor so that the light beam impinges upon the interface in the form of p-polarized light or p-polarized components are only detected.

When the wave number of the surface plasmon can be known from the angle of incidence $\theta sp$ at which the phenomenon of attenuation in total internal reflection (ATR) takes place, the dielectric constant of the sample can be obtained. That is, $$K_{sp}(\omega) = \frac{\omega}{c} \sqrt{\frac{\varepsilon_m(\omega)\varepsilon_s}{\varepsilon_m(\omega) + \varepsilon_s}}$$

wherein $K_{sp}$ represents the wave number of the surface plasmon, $\omega$ represents the angular frequency of the surface plasmon, c represents the speed of light in a vacuum, and $\in m$ and $\in s$ respectively represent the dielectric constants of the metal and the sample.

When the dielectric constant $\in s$ of the sample is known, the concentration of a specific material in the sample can be determined on the basis of a predetermined calibration curve or the like. Accordingly, the specific material in the sample can be quantitatively analyzed by detecting the angle of incidence $\theta sp$ at which the intensity of light reflected in total internal reflection from the interface of the prism and the metal film sharply drops (this angle $\theta sp$ is generally referred to as "the attenuation angle $\theta sp$").

As a similar apparatus utilizing the phenomenon of attenuation in total internal reflection (ATR), there has been known a leaky mode sensor described in, for instance, "Surface Refracto-Sensor using Evanescent Waves: Principles and Instrumentations" by Takayuki Okamoto (Spectrum Researches, Vol.47, No.1 (1998), pp21 to 23 & pp26 and 27). The leaky mode sensor basically comprises a dielectric block shaped, for instance, like a prism, a clad layer which is formed on one face of the dielectric block, an optical waveguide layer which is formed on the clad layer and is brought into contact with a sample, a light source emitting a light beam, an optical system which causes the light beam to enter the dielectric block so that total internal reflection conditions are satisfied at the interface of the dielectric block and the metal film and various angles of incidence of the light beam to the interface including an angle of incidence at which attenuation in total internal reflection is generated due to optical waveguide mode excitation can be obtained, and an information obtaining means which detects the intensity of the light beam reflected in total internal reflection at the interface and obtains information on the state of waveguide mode excitation that is, the attenuation angle or the change thereof.

In the leaky mode sensor with this arrangement, when the light beam is caused to impinge upon the clad layer through the dielectric block at an angle not smaller than an angle of total internal reflection, evanescent waves are generated in the optical waveguide layer and an evanescent wave having a particular wave number comes to propagate through the optical waveguide layer in a waveguide mode. When the waveguide mode is thus excited, almost all the incident light which generates the evanescent wave having a particular wave number is taken in the optical waveguide layer and accordingly, the intensity of light reflected in total internal reflection at the interface of the dielectric block and the clad layer sharply drops. That is, attenuation in total internal reflection occurs. Since the wave number of light to be propagated through the optical waveguide layer depends upon the refractive index of the sample on the optical waveguide layer, the refractive index and/or the properties of the sample related to the refractive index can be detected on the basis of the attenuation angle θsp at which the attenuation in total internal reflection occurs.

Such a measuring apparatus is employed, as a biosensor, to analyze a sample, that is, a sensing medium (e.g. antibody), which combines with a particular material (e.g., antigen), is disposed on the thin film (the metal film in the case of a surface plasmon resonance sensor, and optical waveguide layer in the case of a leaky mode sensor) and whether the sample includes a material combined with the sensing medium or the state of combination of the sample with the sensing medium is detected. As a method of analyzing a sample in this way, there has been proposed a method in which, in order to eliminate the influence of the solvent in the sample liquid on the refractive index of the sample liquid, refractive index information on buffer (the same as the solvent) free from the analyte (material to be analyzed) is first obtained and then the sample liquid is dispensed to the buffer to measure the refractive index information of the mixture after the reaction, whereby only the reaction of the analyte is precisely extracted.

As the surface plasmon resonance sensor, there have been known various types of sensors, as well as those in which the attenuation angle is detected, such as those in which light beams of different wavelengths are caused to impinge upon the interface and the degree of attenuation in total internal reflection is detected by the wavelength, or in which a light beam is caused to impinge upon the interface and a part of the light beam is split before the light beam impinges upon the interface and caused to interfere with the other part of the light beam reflected at the interface, thereby measuring the state of interference. Any one of the sensors is a sensor which indirectly obtains information on the refractive index of the analyte on the thin film or the change thereof and analyzes the analyte.

In order to increase efficiency of handling, for instance, in changing the sample in the measuring apparatus, there has been proposed in U.S. Patent Laid-Open No. 20010040680 a sensor unit comprising a dielectric block, a thin film disposed on the upper surface of the dielectric block and a sample holding portion for holding the sample on the thin film, which are formed integrally with each other. The sensor unit is formed by providing a unit body in the form of a dielectric block with a sample well (sample holding portion) open in the upper surface, and by providing a film layer on the inner bottom surface of the sample well, and the part of the unit body below the sample well functions as the known dielectric block which performs the duty of the light beam input-out system. In order to perform measurement on a number of samples at high speed, and to further increase efficiency of handling, there has been proposed a sensor unit formed by providing a unit body in the form of a bar-like or plate-like dielectric block with a plurality of one-dimensionally or two-dimensionally arranged sample wells. A plurality of light beams are caused to impinge upon the plurality of sample wells in parallel and the reflected light reflected at the interface of each of the sample wells is separately detected.

It is sometimes necessary to perform measurement a plurality of times on a sample at intervals and to detect the change of the state including whether the analyte is bonded with the sensing material. In such a case, in order to perform such measurement on a plurality of samples at high efficiency, there sometimes employed batch processing in which a first sensor unit is once demounted from the measuring portion (sensor holding portion) of a measuring apparatus after a first measurement on the sample placed in its sample well, another or a second sensor unit is mounted on the measuring portion of the measuring apparatus, and then the first sensor unit is mounted again on the measuring portion of the measuring apparatus after measurement on the samples placed in the sample wells of the second senor well unit. Conventionally, there has been a problem that the position of the interface changes each time the same sensor unit is mounted on the measuring portion, which can result in a measuring error.

As a method of dealing with this problem, there has been proposed a method in which displacement of the sensor unit is measured with the outer surfaces of the sensor unit taken as a reference plane, and the position of the sensor unit is adjusted on the basis of the measured displacement.

However, these inventor's investigation has revealed that even if the position of the sensor unit is adjusted in this manner, there still remains a measuring error (an error produced when the state of light reflected in total internal reflection is measured) due to displacement of the interface due to thermal expansion of the sensor unit.

SUMMARY OF THE INVENTION

In view of the foregoing observations and description, the primary object of the present invention is to provide a measuring apparatus in which deterioration of measuring accuracy due to thermal expansion of the sensor unit is suppressed and the measuring accuracy is high.

In accordance with the present invention, there is provided a first measuring apparatus comprising a sensor unit comprising a dielectric block, a thin film layer which is formed on the upper surface of the dielectric block, and a sample holding portion which holds a sample on the thin film layers a light source emitting a light beam, a sensor holding means which demountably holds the sensor unit in a predetermined position, a light beam projecting means which causes the light beam to enter the dielectric block to impinge upon the interface between the upper surface of the dielectric block and the thin film layer so that total internal reflection conditions are satisfied at the interface, a measuring means provided with a refractive index information obtaining means which obtains refractive index information on analyte on the thin film layer on the basis of the light beam reflected at the interface, a measuring system which accommodates the measuring means, a temperature measuring means which measures the temperature of the measuring system, a constant temperature system which is controlled to be at a predetermined temperature and stores the sensor unit, a conveyor means which selectively positions the sensor unit in a predetermined position in the measuring system or in the constant temperature system, and a controlling means which controls the measuring means and the conveyor means, wherein the improvement comprises that the controlling means estimates temperature change of the sensor unit after it is conveyed to the measuring system from the constant temperature system on the basis of the temperature difference between the predetermined temperature and the measured temperature of the measuring system as measured by the temperature measuring means, and drives the conveyor means to convey the sensor unit to the measuring system and the measuring means to perform the measurement within a time for which the temperature of the sensor unit does not change from the predetermined temperature by a temperature range which is larger than an acceptable temperature range.

In accordance with the present invention, there is provided a second measuring apparatus comprising a sensor unit comprising a dielectric block, a thin film layer which is formed on the upper surface of the dielectric block, and a sample holding portion which holds a sample on the thin film layer a light source emitting a light beam, a sensor holding means which demountably holds the sensor unit in a predetermined position, a light beam projecting means which causes the light beam to enter the dielectric block to impinge upon the interface between the upper surface of the dielectric block and the thin film layer so that total internal reflection conditions are satisfied at the interface, a measuring means provided with a refractive index information obtaining means which obtains refractive index information on analyte on the thin film layer on the basis of the light beam reflected at the interface, a measuring system which accommodates the measuring means, a temperature measuring means which measures the temperature of the measuring system, a constant temperature system which is controlled to be at a predetermined temperature and stores the sensor unit, a conveyor means which selectively positions the sensor unit in a predetermined position in the measuring system or in the constant temperature system, and a controlling means which controls the measuring means and the conveyor means, wherein the improvement comprises that the controlling means estimates temperature change of the sensor unit after it is conveyed to the measuring system from the constant temperature system on the basis of the temperature difference between the predetermined temperature and the measured temperature of the measuring system as measured by the temperature measuring means, and drives the conveyor means to convey the sensor unit to the measuring system and the measuring means to perform the measurement in a time range for which the temperature of the sensor unit is kept in a particular temperature range.

Conventionally, though displacement of the sensor unit is measured with the outer surfaces of the sensor unit taken as a reference plane, and the position of the sensor unit is adjusted on the basis of the measured displacement as described above, these inventor's investigation has revealed that there still remains a measuring error due to displacement of the interface due to thermal expansion of the sensor unit since the interface differs from the reference plane in position. For example, it is necessary for the displacement of the sensor unit in the horizontal direction (parallel to the interface) to be not larger than 0.3 μm when the accuracy in detecting the angle of reflection of the reflected light measured by the photodetector in an actual measuring apparatus is to be within 0.00001° (0.1 RU). In this case, the acceptable temperature change of the sensor unit is not larger than 0.065° C. (in the case of ZEONEX:E48R). However, it is difficult at present to control the temperature of the sensor unit itself, and it is also difficult to finely control the temperature of the atmosphere of the measuring apparatus due to existence of heat sources such as the light sources and the sensors.

In accordance with the present invention, a constant temperature system such as an incubator the temperature of which is highly controllable is provided, the measuring means is spatially isolated from the surroundings by placing it in the measuring system, the temperature of the measuring system is measured by the temperature measuring means and temperature change of the sensor unit after it is conveyed to the measuring system from the constant temperature system is estimated by the controlling means on the basis of the temperature difference between the temperature of the constant temperature system (the predetermined temperature) and the measured temperature of the measuring system, and the conveyor means and the measuring means is driven by the controlling means to convey the sensor unit to the measuring system to perform the measurement within a time for which the temperature of the sensor unit does not change from the predetermined temperature by a temperature range which is larger than an acceptable temperature range or in a time range for which the temperature of the sensor unit is kept in a particular temperature range, whereby fluctuation in temperature of the sensor unit upon measurement is suppressed and deterioration in measuring accuracy is prevented. With this arrangement, the temperature of the sensor unit upon measurement can be accurately controlled irrespective of relatively rough temperature control in the measuring system.

In the first and second measuring apparatuses of the present invention, the thin film layer may be of metal film. In this case, the measuring apparatus is a surface plasmon resonance sensor which measures on the basis of the surface plasmon resonance. Further, in the first and second measuring apparatuses, the thin film layer may comprise a clad layer formed on the upper surface of the dielectric block and an optical waveguide layer which is formed on the clad layer. In this case, the measuring apparatus is a leaky mode sensor which measures on the basis of the effect of excitation of waveguide mode in the waveguide layer.

The expression "to obtain refractive index information on analyte" should be broadly interpreted to include both "to obtain the refractive index of the sample disposed on the thin film layer" and "to fix on the thin film layer a sensing medium such as an antibody and to detect change in the refractive index of the sample containing therein the analyte such as antigen due to reaction of the sensing material with the analyte such as antigen-antibody reaction or to detect whether or not there is change of the refractive index due to reaction of the sensing material with the analyte such as antigen-antibody reaction.

The refractive index information may be obtained by obtaining the refractive index or the change of the refractive index by causing a light beam to impinge upon the interface at various angles of incidence and detecting light beams reflected at the interface to detect the attenuation angle or change thereof or by obtaining the refractive index or the change of the refractive index by wavelengths by causing a plurality of light beams having different wavelengths to impinge upon the interface so that total internal reflection conditions are satisfied at the interface, measuring the intensities of the light beams reflected in total internal reflection at the interface by wavelengths and detecting the degree of attenuation in total internal reflection by wavelengths as disclosed in "Porous Gold in Surface Plasmon Resonance Measurement" by D. V. Noort, K. Johansen, and C. F.

Mandenius (EUROSENSORS X III, 1999, pp.585–588). Further, the refractive index information may be obtained by obtaining the change of the refractive index by causing a light beam to impinge upon the interface so that total internal reflection conditions are satisfied at the interface, splitting a part of the light beam before impinging upon the interface, causing the part of the light beam to interfere with the light beam reflected in total internal reflection at the interface, and detecting change of the interference fringe in the light beam after the interference as disclosed in "Surface Plasmon Resonance Interferometry for Micro-Array Biosensing" by P. I. Nikitin, A. N. Grigorenko, A. A. Beloglazov, M. V. Valeico, A. I. Savchuk, and O. A. Savchuk (EUROSENSORS X III, 1999, pp.235–238).

That is, the "refractive index information on analyte" may be any so long as it changes with change of the refractive index of the analyte, and may be, for instance, an attenuation angle or a wavelength of the light beam generating attenuation in total internal reflection which changes with change of the refractive index of the analyte, change of the attenuation angle or the wavelength of the light beam generating attenuation in total internal reflection or the change of the aforesaid interference fringe.

In the first measuring apparatus of the present invention, since a constant temperature system such as an incubator the temperature of which is highly controllable is provided, the measuring means is spatially isolated from the surroundings by placing it in the measuring system, the temperature of the measuring system is measured by the temperature measuring means and temperature change of the sensor unit after it is conveyed to the measuring system from the constant temperature system is estimated by the controlling means on the basis of the temperature difference between the temperature of the constant temperature system (the predetermined temperature) and the measured temperature of the measuring system, and the conveyor means and the measuring means is driven by the controlling means to convey the sensor unit to the measuring system to perform the measurement within a time for which the temperature of the sensor unit does not change from the predetermined temperature by a temperature range which is larger than an acceptable temperature range, fluctuation in temperature of the sensor unit upon measurement can be suppressed and accordingly deterioration in measuring accuracy can be prevented.

In the second measuring apparatus of the present invention, since a constant temperature system such as an incubator the temperature of which is highly controllable is provided, the measuring means is spatially isolated from the surroundings by placing it in the measuring system, the temperature of the measuring system is measured by the temperature measuring means and temperature change of the sensor unit after it is conveyed to the measuring system from the constant temperature system is estimated by the controlling means on the basis of the temperature difference between the temperature of the constant temperature system (the predetermined temperature) and the measured temperature of the measuring system, and the conveyor means and the measuring means is driven by the controlling means to convey the sensor unit to the measuring system to perform the measurement in a time range for which the temperature of the sensor unit is kept in a particular temperature range, fluctuation in temperature of the sensor unit upon measurement can be suppressed and accordingly deterioration in measuring accuracy is prevented.

BRIEF DESCRIPTION OF THE DRAWINGS

FIGS. 4A to 4C are a plan view, a front view and a side view schematically showing the positional relation between the sensor unit and the electrostatic probes and the optical angle displacement meter in the surface plasmon resonance sensor, FIGS. 7A and 7B are views representing the temperature change of the sensor unit when it is conveyed from the constant temperature system to the measuring system in one embodiment of the present invention.

DESCRIPTION OF THE PREFERRED EMBODIMENTS

Figure 1:
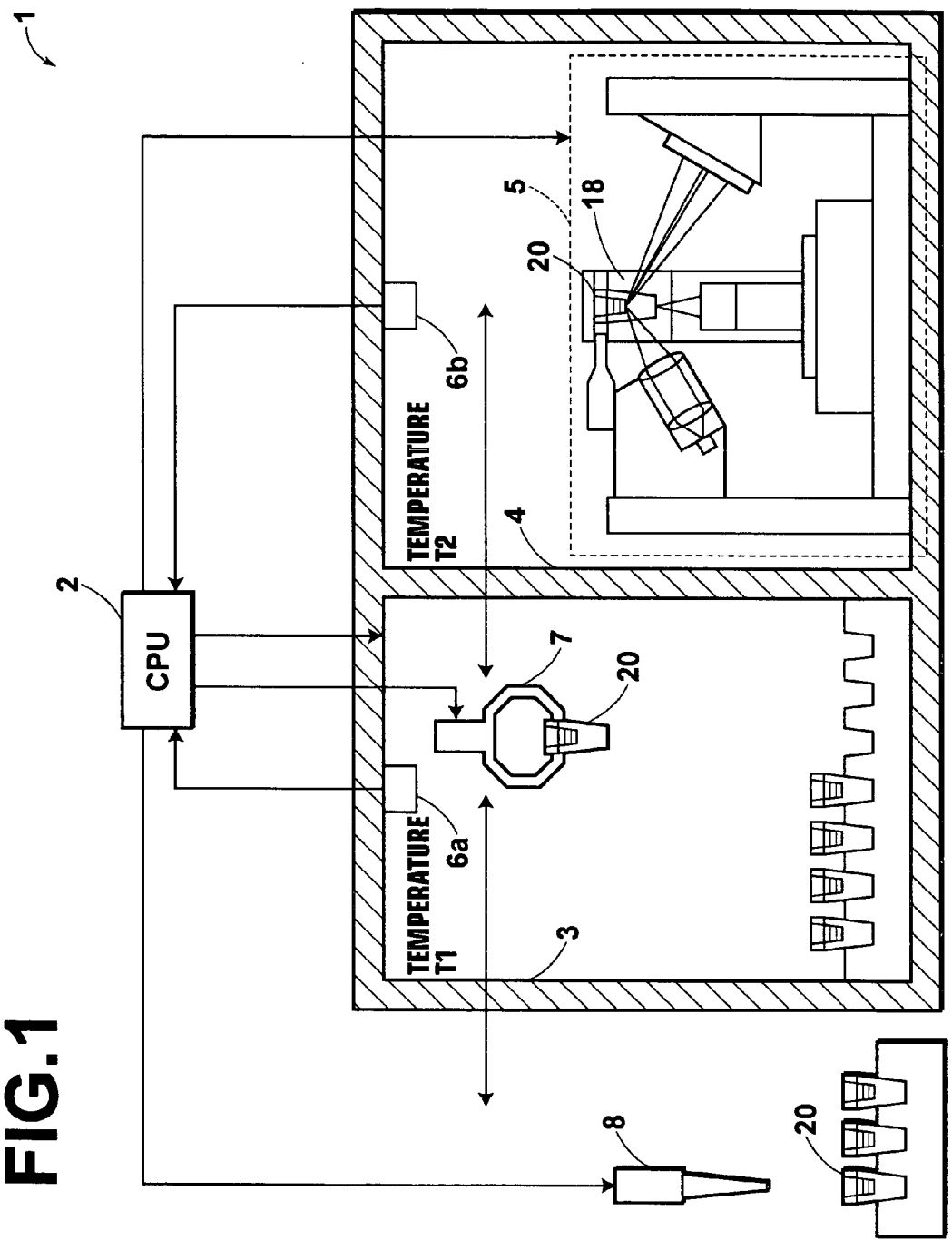
FIG. 1 is a view showing a measuring apparatus in accordance with a first embodiment of the present invention.

In FIG. 1, a measuring apparatus 1 in accordance with a first embodiment of the present invention comprises a sensor unit 20 to which a sample is dispensed, a surface plasmon resonance sensor 5 which analyzes the sample dispensed to the sensor unit 20, a measuring system 4 which accommodates the measuring means (the surface plasmon resonance sensor) 5, a constant temperature system 3 which is controlled to be at a predetermined temperature and stores the sensor unit 20, a temperature sensor 6a which measures the temperature of the measuring system, a temperature sensor 6b which measures the temperature of the measuring system 4, a conveyor means 7 which selectively positions the sensor unit 20 in a predetermined position in the measuring system 4 or in the constant temperature system 3, a dispenser 8 which dispenses the sample to the sensor unit 20, and a CPU (controlling means) 2 which controls the surface plasmon resonance sensor 5, the conveyor means 7 and the dispenser 8.

As shown in FIGS. 3 and 4A–4C, the sensor unit 20 is provided with a body 21 formed of an elongated transparent dielectric material and a plurality of (e.g., 16) sample wells 23 are formed in the body 21 in a predetermined depth to open in the upper surface 21a of the body 21. The sample wells 23 are arranged in a row and metal film 12 is coated on the inner bottom surface 23a of each of the sample wells 23 by deposition. That is, the body 21 comprises a dielectric block 22 transparent to a light beam (to be described later) and a sample holding portion which forms the side surface of each sample well 23, which are formed integrally with each other, and the upper surface of the dielectric block 22 forms the inner bottom surface 23a of each of the sample wells 23. Accordingly, the metal film 12 coated on the inner bottom surface 23a of each of the sample wells 23 is equivalent to metal film coated on the upper surface of the dielectric block 22, and the interface between the inner bottom surface 23a of each sample well 23 and the metal film 12 corresponds to the interface between the upper surface of the dielectric block 22 and the metal film 12. The outer bottom surface 21c (FIG. 3) of the body 21 of the sensor unit 20 is taken as a reference surface for position measurement.

The body 21 is formed, for instance, of transparent synthetic resin. Each sample well 23 is circular in cross-section and the diameter of each sample well 23 is reduced downward. In this particular embodiment, a sensing medium 14, which is combined with a particular material, is fixed on the metal film 12. Sample liquid containing therein an analyte is stored in each sample well 23.

As shown in FIGS. 4A–4C, first and second flanges 24 and 25 which are the same in thickness project outward respectively from the left and right ends of the body 21. The flanges 24 and 25 have upper surfaces 24a and 25a flush with the upper surface 21a of the body 21 and lower surfaces 24b and 25b parallel respectively to their upper surfaces 24a and 25a.

Further detail regarding the positioning of the various element of the measuring apparatus are explained below with regard to FIGS. 2, 3 and 4A–4C. The surface plasmon resonance sensor 5 comprises a platen 17, a sensor holding means 18 which is disposed on a six-axis fine-movement stage 38 to be described later and demountably holds the sensor unit 20 in a predetermined position above the platen 17, light sources 50A, 50B, . . . 50P which are the same in number as the sample wells 23 and each of which emits a light beam L, light beam projecting means 60A, 60B, . . . 69P which cause the light beam L emitted from each of the light sources 50A, 50B, . . . 50P to enter the dielectric block to impinge upon the interface 23b between the upper surface of the dielectric block 22 and the thin film layer (metal film) 12 on the inner bottom surface 23a of the sample well 23 at various angles of incidence so that total internal reflection conditions are satisfied at the interface 23b, photodetectors 70A, 70B, . . . 70P each of which detects the intensity of the light beam L reflected at the interface 23b, a signal processing system 10 which may be of a computer system and obtains attenuation information on the basis of the outputs of the photodetectors 70A, 70B, . . . 70P, a display means 11 connected to the signal processing system 10, a displacement measuring means 30 which measures displacement of the sensor unit 20 and a position adjustment means which comprises a six-axis fine-movement stage 38 disposed on the platen 17 and a drive means 39 which outputs a signal for driving the stage 38 and mechanically adjusts the position of the sensor unit 20. In this particular embodiment, the photodetectors 70A, 70B, . . . 70P and the signal processing system 10 form the attenuation information obtaining means which is an example of the refractive index information obtaining means.

In this embodiment, a plane parallel to the platen 17 is referred to as "XYw plane", the direction in which the light beam projecting means 60 (60A, 60B, . . . 60P), the sensor holding means 18 and the photodetector 70 (70A, 70B, . . . 70P) are arranged in the XYw plane is referred to as "Yw axis direction", a direction perpendicular to the Yw axis direction is referred to as "Xw axis direction" and a direction perpendicular to the XYw plane is referred to as "Zw axis direction". Further, the direction of rotation about the Xw axis or in the YZw plane is denoted by $\theta w$, the direction of rotation about the Yw axis or in the ZXw plane is denoted by $\phi w$, and the direction of rotation about the Zw axis or in the XYw plane is denoted by $\psi w$.

The six-axis fine-movement stage 38 has six axes in the Xw direction, the Yw direction, the Zw direction and directions of rotation $\theta w$, $\phi w$ and $\psi w$ and disposed so that the axes conforms to those determined on the basis of the platen 17.

The sensor holding means 18 supports the lower surfaces 24b and 25b of the first and second flanges 24 and 25 of the sensor unit 20 and supports the sensor unit 20 in a predetermined position above the platen 17 so that the sample wells 23 are arranged substantially along the Xw direction and the vertical displacement of the sensor unit 20 to the platen 17 is the displacement of the sensor unit 20 in the Zw direction. (FIGS. 2 and 3)

The light beam projecting means 60 (60A, 60B, . . . 60P) and the photodetector 70 (70A, 70B, . . . 70P) are fixed to the platen 17 by way of fixing portions 2a and 2b on opposite sides of the sensor holding means 18. Each of the light beam projecting means 60A, 60B, . . . 6P and each of the photodetectors 70A, 70B, . . . 70P are positioned to be aligned with one of the 16 sample wells 23.

Each of the light beam projecting means 60A, 60B, . . . 60P comprises a collimator lens 61 which converts the light beam L, emitted from the corresponding laser light source 50A, 50B, . . . 50P as a divergent light beam, into a parallel light, and a condenser lens 62 which condenses the light beam L.

Figure 2:
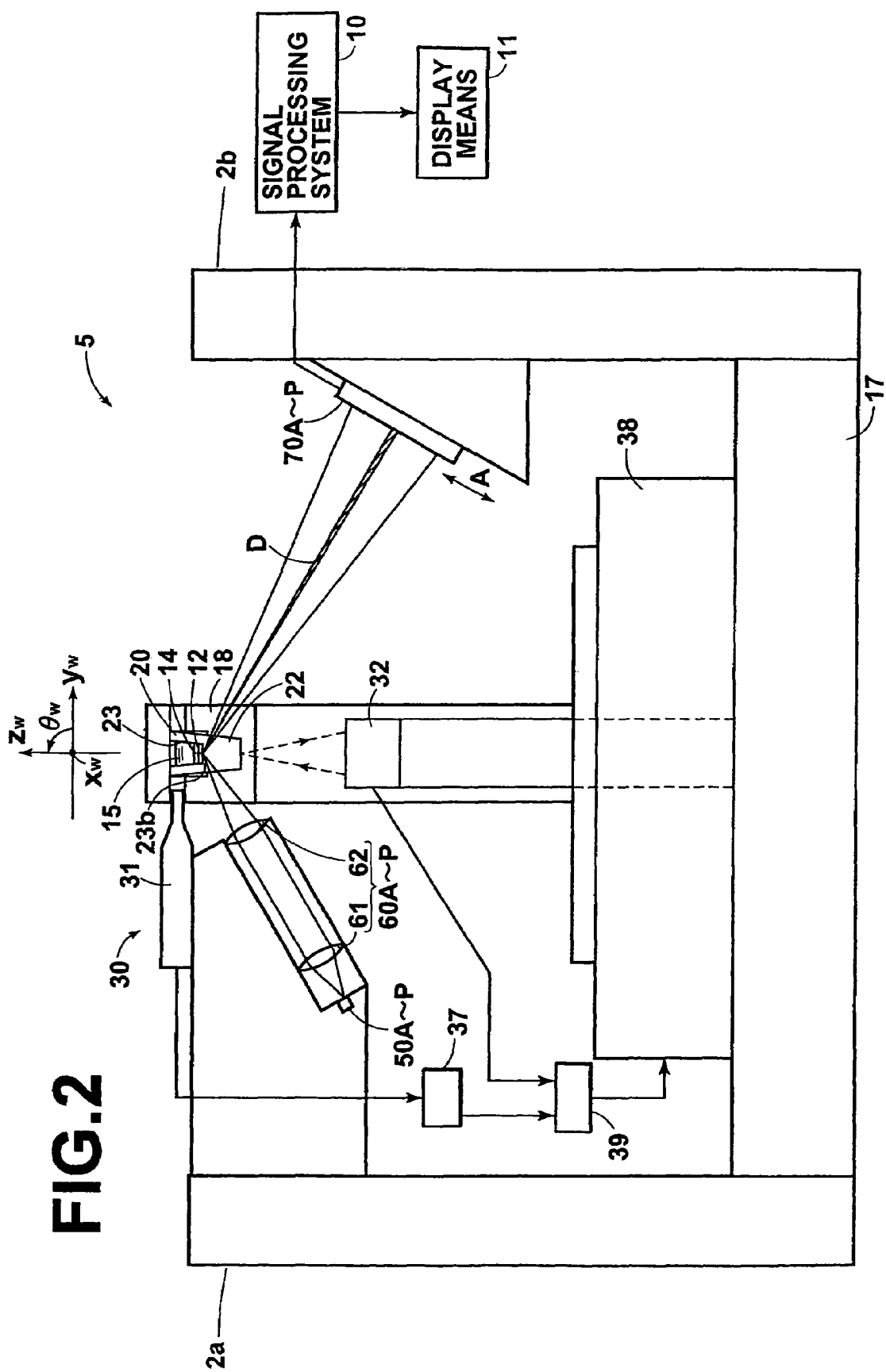
FIG. 2 is a side cross-sectional view of a surface plasmon resonance sensor and the sensor unit of the measuring apparatus of the first embodiment of the present invention.
Figure 3:
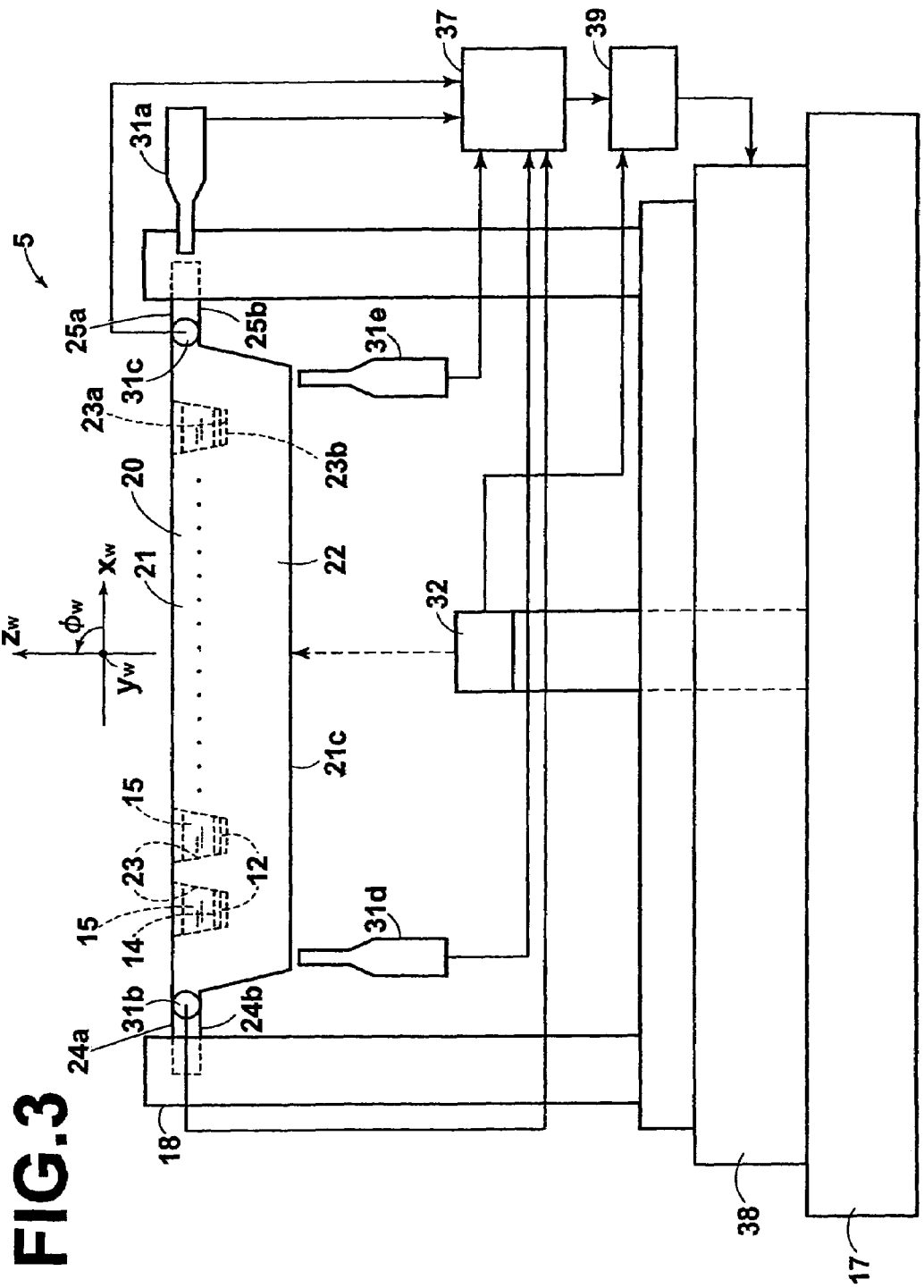
FIG. 3 is a front view of the same.

The photodetector 70A comprises a line sensor formed of a plurality of photosensor elements which are arranged in a row extending in a direction perpendicular to the direction in which light beam L travels (the direction indicated by arrow A in FIG. 2). The line sensor may be a photodiode array or a CCD line sensor and the photodetector may comprise two-part photodiodes.

The displacement measuring means 30 comprises five electrostatic probes 31a to 31e and an optical angle displacement meter 32 which are fixed with respect to the platen 17, and a console 37 which controls the electrostatic probes 31a to 31e and measures displacements of the sensor unit 20 in the Xw direction, the Yw direction, the Zw direction and the directions of rotation $\theta w$, $\phi w$ and $\psi w$.

As shown in FIGS. 4A to 4C, the sensor unit 20 is disposed so that the longitudinal direction of the sensor unit 20 extends along the Xw axis and the upper surface of the sensor unit 20 extends in perpendicular to the Zw axis.

The electrostatic probe 31a disposed to face a side surface 25d of the second flange 25 of the sensor unit 20 (FIG. 4A) is for measuring the displacement of the sensor unit 20 in the direction of the Xw axis, and the electrostatic probes 31b and 31c facing the side surfaces 24c and 25c of the first and second flanges 24 and 25 of the sensor unit 20 (FIG. 4A) are for measuring the displacement of the sensor unit 20 in the direction of the Yw axis. On the basis of the outputs of the electrostatic probes 31b and 31c, displacement of the sensor unit 20 from the reference position in the $\phi w$ direction (the angle of rotation) can be known.

The electrostatic probes 31*d* and 31*e* facing the reference surface 21*c* (the outer bottom surface) of the body 21 of the sensor unit 20 (FIG. 4B) are for measuring the displacement of the sensor unit 20 in the direction of the Zw axis. On the basis of the outputs of the electrostatic probes 31*d* and 31*e*, displacement of the sensor unit 20 from the reference position in the $\phi$w direction (the angle of rotation) can be known.

The electrostatic probes 31*a* to 31*e* which measure electrostatic capacity are generally 0.5 mm in diameter and ±25 µm in measuring full scale. However, the diameter and the measuring full scale of the electrostatic probes need not be limited to these values.

The console 37 generates electrostatic capacity between the sensor on the tip of the electrostatic probes 31*a* to 31*e* and the surface and detects displacement of the surface as a change of the electrostatic capacity on the basis of the fact that the electrostatic capacity changes with the distance between the surface and the sensor, and outputs the displacement of the surface in terms of electric voltages. The reference surface 21*c* (the outer bottom surface) of the body 21 of the sensor unit 20 and the side surfaces 24*c*, 25*c* and 25*d* of the first and second flanges 24 and 25 of the sensor unit 20 the distances to which are to be measured are coated with metal film, e.g., of gold by deposition.

The optical angle displacement meter 32 positioned below the center of the sensor unit 20 in the Xw direction (FIG. 4C) is an optical lever type sensor, which detects displacement of the sensor unit 20 from the reference position in the θw direction (the angle of rotation) by causing a light beam to impinge upon the reference surface 21*c* of the sensor unit 20 at the center of the sensor unit 20 in the Xw direction and receiving the light beam reflected thereat. The part of the reference surface 21*c* of the sensor unit 20 at which the light beam impinges upon the sensor unit 20 is coated with metal film, e.g., of gold by deposition to form a mirror surface.

The drive means 39 outputs a signal for driving the stage 38 according to the displacement measured by the displacement measuring means 30 to return the sensor unit 20 to the reference position.

The six-axis fine-movement stage 38 is driven upon receipt of the output of the drive means 39, and the position of the sensor holding means 18 on the stage 38 is finely adjusted to adjust the position of the interface of the sensor unit 20 held by the sensor holding means 18.

In the conventional apparatus, displacement of the sensor unit is measured with the outer surfaces of the sensor unit taken as a reference plane, and the position of the sensor unit is adjusted on the basis of the measured displacement as described above. However, since the interface which is an actual measuring surface differs in position from the outer surface, a measuring error (an error generated when the state of the light reflected in total internal reflection is measured) is caused due to displacement of the interface due to thermal expansion of the sensor unit For example, it is necessary for the displacement of the sensor unit in the horizontal direction (parallel to the interface) to be not larger than 0.3 µm when the accuracy in detecting the angle of reflection of the reflected light measured by the photodetector in an actual measuring apparatus is to be within 0.00001° (0.1 RU). In this case, the acceptable temperature change of the sensor unit is not larger than 0.065° C. (in the case of ZEONEX: E48R). However, it is difficult at present to control the temperature of the sensor unit itself, and it is also difficult to finely control the temperature of the atmosphere of the measuring apparatus.

In accordance with this embodiment, a constant temperature system 3 the temperature of which is highly controllable is provided, the surface plasmon resonance sensor (the measuring means) 5 is spatially isolated from the surroundings by placing it in the measuring system 4, the temperature of the measuring system 4 is measured by the temperature sensor 6*b* and temperature change of the sensor unit 20 after it is conveyed to the measuring system 4 from the constant temperature system 3 is estimated by the CPU 2 on the basis of the temperature difference between the temperature of the constant temperature system 3 (the predetermined temperature) and the measured temperature of the measuring system 4, and the sensor unit 20 is conveyed to the measuring system to perform the measurement within a time for which the temperature of the sensor unit 20 does not change from the predetermined temperature by a temperature range which is larger than an acceptable temperature range, whereby fluctuation in temperature of the sensor unit 20 upon measurement is suppressed and deterioration in measuring accuracy is prevented.

The method of CPU 2 estimating the temperature change of the sensor unit 20 after it is conveyed to the measuring system 4 from the constant temperature system 3 will be described hereinbelow.

Under the existence of a temperature gradient, a heat flow represented by the following formula (1) is generally generated from the sensor unit (at a temperature T2) to the exterior (at a temperature T1) or from the exterior (at a temperature T1) to the sensor unit (at a temperature T2).

$$q = hA\Delta T = -c\rho V dT/dt \quad (1)$$

wherein, h represents the heat transfer coefficient (W/m²·K), A represents the surface area (m²), c represents the specific heat (J/g·K), ρ represents the density (kg/m³) and V represents the volume (m³). The thermal resistance Rth and the heat capacity Cth are represented respectively by 1/hA and cρV and depend upon the quality, shape and size of the material and the temperature difference between the material and the surroundings. Further, the temperature Tw of the sensor unit 20 changes with time as represented by the following formula (2).

$$Tw = T2\exp(-t/\tau) \quad (2)$$

wherein τ(=Rth·Cth) is so-called a thermal time constant and represents the time required for the temperature change reaches 63.2% of the stationary value.

Figure 5:
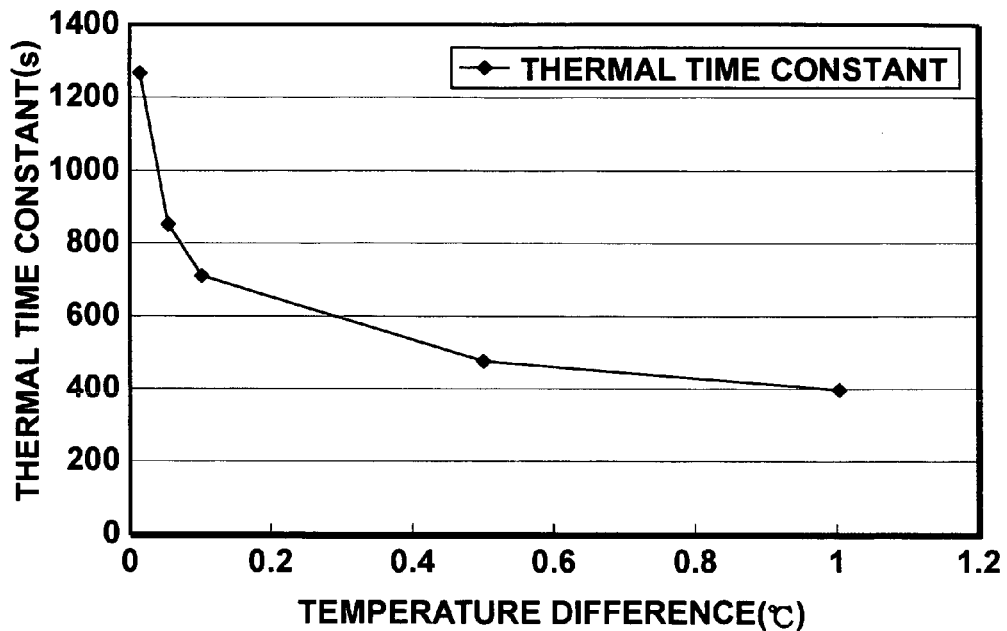
FIG. 5 is a view showing the relation between the temperature difference and the thermal time constant in the sensor unit.

For example, when the sensor unit 20 is of E48R (ZEONEX) and is of a size of 74 mm×4.4 mm×9 mm (length×width×height), the thermal time constant of the sensor unit 20 is a function of ΔT as shown in FIG. 5.

Figure 6:
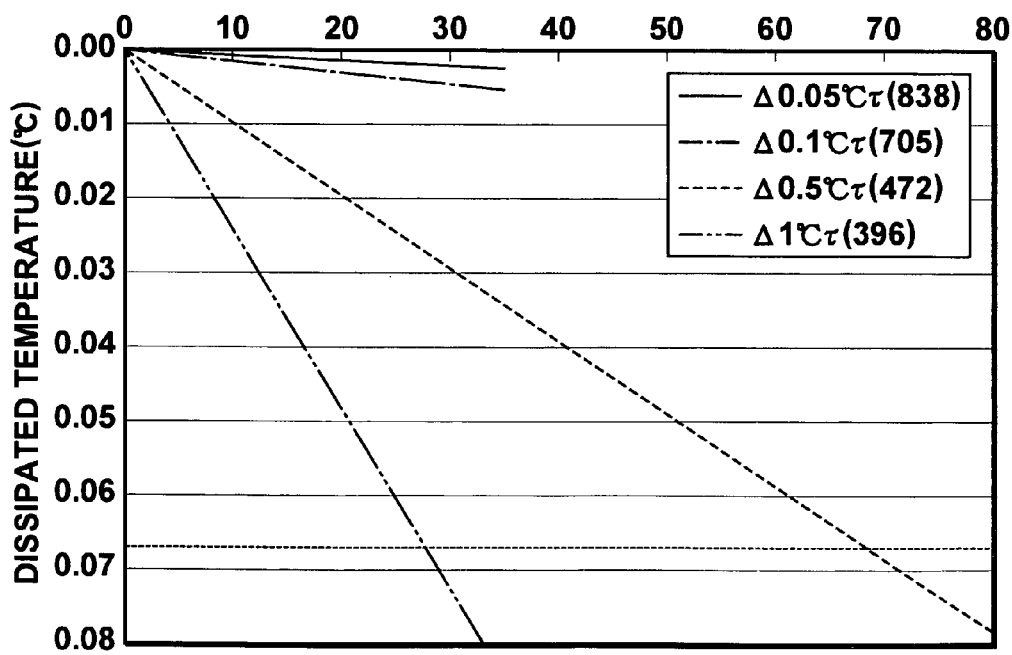
FIG. 6 is a view showing the relation between the dissipated temperature and the time when ZEONEX:E48R is employed as the sensor unit.

On the basis of the formula (2) and the thermal time constant, the temperature change of the sensor unit 20 after it is conveyed from the constant temperature system 3 (at a temperature T2) to the measuring system 4 (at a temperature T1) can be estimated as shown in FIG. 6.

Since the time $T_{limit}$ for which the temperature of the sensor unit 20 does not change from the predetermined temperature T2 of the constant temperature system 3 by a temperature range which is larger than an acceptable temperature range can be determined on the basis of the temperature change of the sensor unit 20, fluctuation in temperature of the sensor unit 20 upon measurement is suppressed and deterioration in measuring accuracy is prevented by effecting each measurement (from conveyance of the sensor unit 20 from the constant temperature system 3 to the measuring system 4 to finish of the measurement) within the time $T_{limit}$ as shown in FIG. 7A when batch processing is to be carried out.

For example, when the accuracy in detecting the angle of reflection of the reflected light measured by the photodetector is to be within 0.00001° (0.1 RU), the acceptable temperature change of the sensor unit is not larger than 0.065° C. and it is necessary to finish the measurement within 28 seconds after the sensor unit 20 is conveyed from the constant temperature system 3 to the measuring system 4 if the temperature difference between the constant temperature system 3 and the measuring system 4 is 1° C. ($\tau$=396).

In the case where the temperature of the measuring system 4 differs from measurement to measurement, that is, when the thermal time constant of the sensor unit 20 changes from measurement to measurement, as shown in FIG. 7B, the time $T_{limit}$ for which the temperature of the sensor unit 20 does not change from the predetermined temperature T2 of the constant temperature system 3 by a temperature range which is larger than an acceptable temperature range also changes from measurement to measurement and accordingly, the time acceptable for the measurement is set according to the time $T_{limit}$ thus determined for the measurement.

Figure 8A:
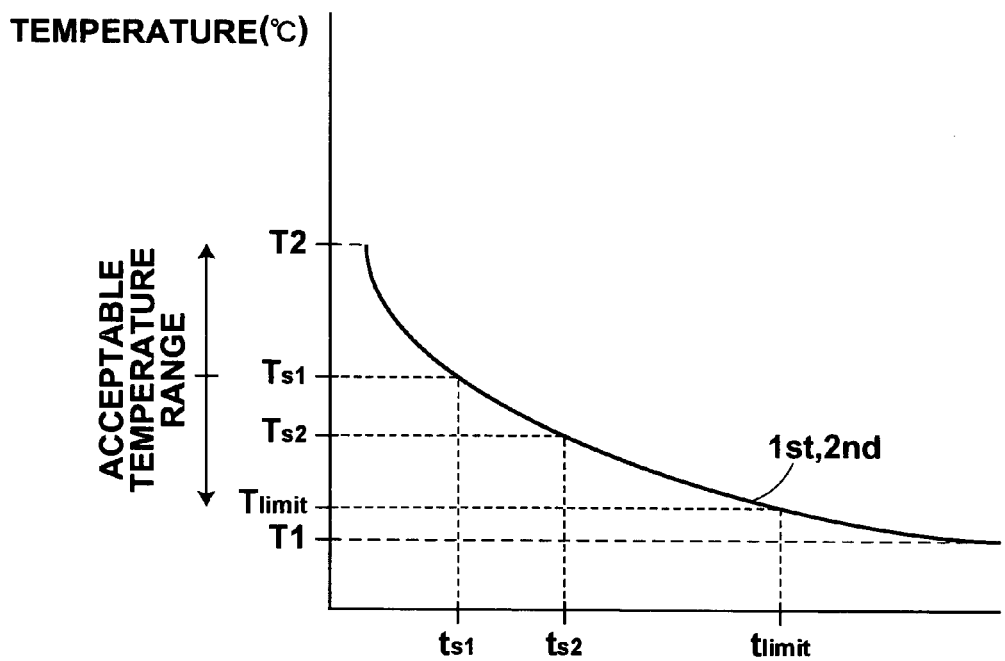
FIGS. 8A and 8B are views representing the temperature change of the sensor unit when it is conveyed from the constant temperature system to the measuring system in another embodiment of the present invention.
Figure 8B:
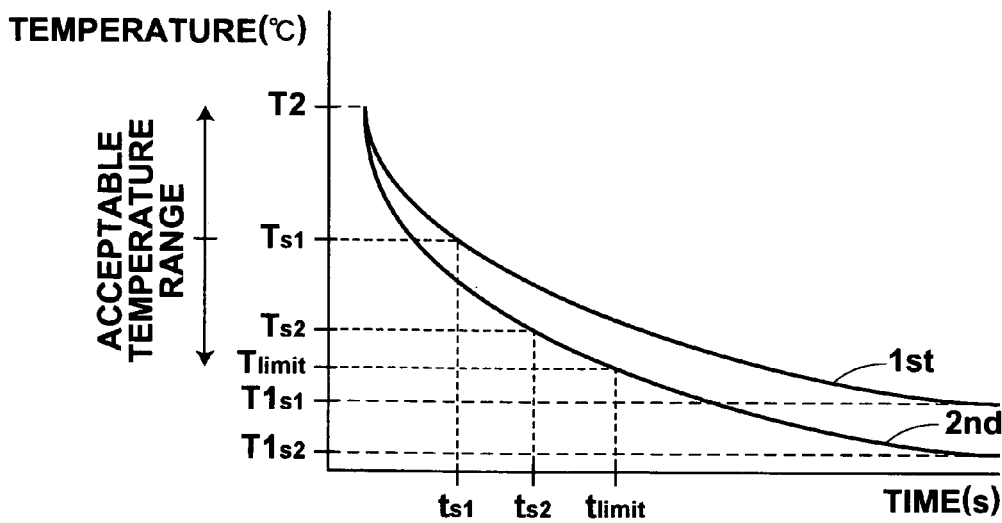

When the batch processing is to be carried out, the same result can be obtained by effecting the next measurement in a time range for which the temperature of the sensor unit is kept in an acceptable temperature range from the temperature Ts1 of the sensor unit 20 upon the first time measurement as shown in FIGS. 8A and 8B.

Sample analysis by the surface plasmon resonance sensor 5 of this embodiment will described, hereinbelow. Analysis of a sample by a sample well 23 in alignment with the light beam projecting means 60A and the photodetector 70A out of the sixteen sample wells 23 in the sensor unit 20 will be described by way of example, hereinbelow. However, analysis of a sample by other sample wells 23 is made in the same manner.

The light source 50A which may be, for instance, a semiconductor laser, is driven and a light beam L is emitted from the light source 50A as a divergent light beam. The light beam L is collimated by a collimator lens 61 of the light beam projecting means 60A and is condensed by a condenser lens 62 to enter the dielectric block 22 as a convergent light beam and to impinge upon the interface 23b between the upper surface of the dielectric block 22 (the inner bottom surface 23a of each sample well 23) and the metal film 12 so that components impinging upon the interface at various angles of incidence of the light beam L to the interface 23b are included therein. The angle of incidence $\theta$ is in a range where total internal reflection conditions of the light beam L are satisfied and surface plasmon resonance is generated at the interfaces 23b. The inner bottom surface 23a of each of the sample wells 23 and the interface 23b may be considered to be substantially in flush with each other.

The light beam L impinging upon the interface 23b is reflected in total internal reflection at the interface 23b and the reflected light beam L is detected by the photodetector 70A. Since the light beam L includes components impinging upon the interface 23b at various angles of incidence, the reflected light beam L includes components reflected at the interface 23b at various angles of reflection. In the photodetector 70A, different photosensor elements receive the components of the light beam L reflected at various angles of reflection and the photodetector 70A outputs a signal representing intensity distribution of the reflected light beam L received by the photosensor elements.

Figure 9:
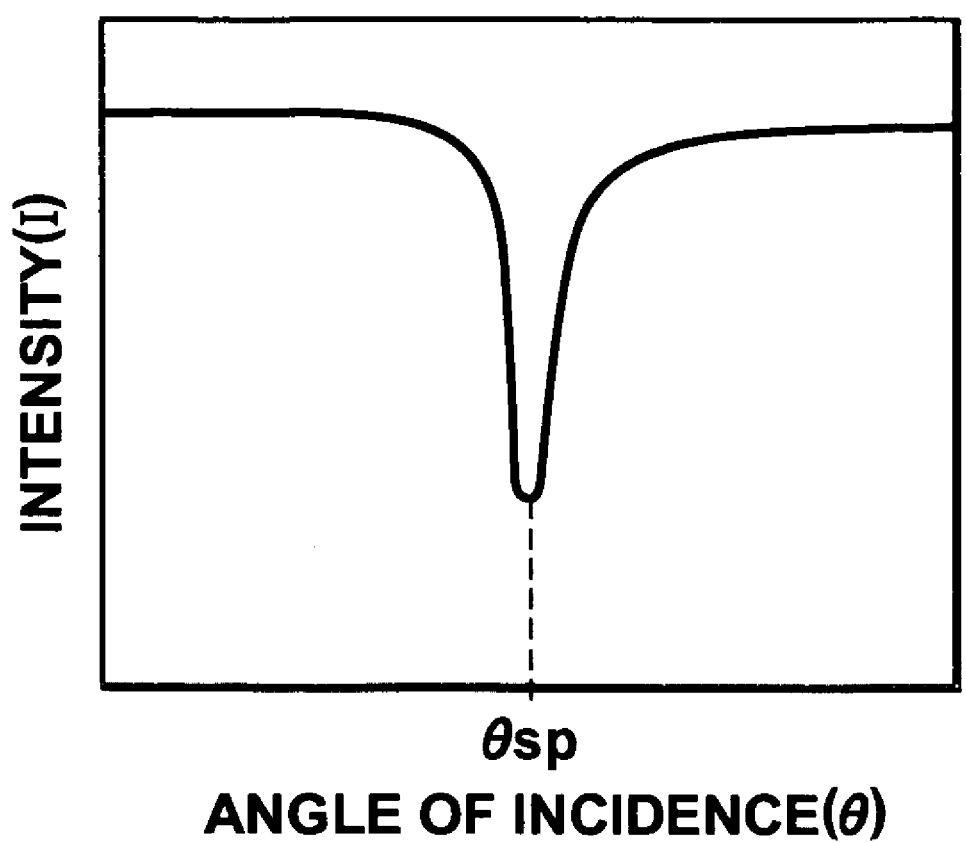
FIG. 9 is a view showing the relation between the angle of incidence θ of the light beam to the interface and the intensity I of the light beam detected by the photodetector.

The component of the light beam L impinging upon the interface 23b at a particular angle of incidence $\theta$sp excites surface plasmon in the interface between the metal film 12 and material in contact with the metal film 12 and the intensity of the component reflected in total internal reflection sharply drops. That is, the particular angle of incidence $\theta$sp is the attenuation angle or the angle at which the total internal reflection is cancelled and the intensity of the reflected light beam exhibits a minimum value at the angle of incidence $\theta$sp. The region where the intensity of the reflected light beam sharply drops is generally observed as a dark line D in the reflected light beam L. By detecting the amount of light detected by the photosensor elements on the basis of the signal output from the photodetector 70A, the attenuation angle $\theta$sp can be obtained on the basis of the position of the photosensor element detecting the dark line. FIG. 9 is a view showing the relation between the angle of incidence $\theta$ of the light beam L to the interface and the intensity I of the light beam received by the photodetector 70A. The attenuation angle $\theta$sp changes with change of the dielectric constant or the refractive index of the material in contact with the metal film 12 and moves right and left with change of the dielectric constant or the refractive index of the material in contact with the metal film 12. The angle of incidence $\theta$ and the particular angle of incidence $\theta$sp are referred to with respect to the angle of incidence of the light beam to the interface and have nothing to do with the $\theta$w direction (the angle of rotation) about the Xw axis described above.

The sensing medium 14 fixed to the surface of the metal film 12 in this embodiment combines a particular material and when a sample liquid containing therein the particular material is dropped on the sensing medium 14, the refractive index of the sensing medium 14 on the metal film 12 changes with change of the state of combination of the particular material with the sensing medium 14 and the curve shown in FIG. 9 moves right and left (that is, the attenuation angle $\theta$sp moves right and left). By measuring change of the attenuation angle $\theta$sp, whether the particular material is contained in the sample liquid can be detected. In this case, both the sample liquid 15 and the sensing medium 14 are the object of analysis. As combinations of such a particular material and a sensing medium, for instance, combinations of an antigen and an antibody have been known.

On the basis of the principle described above, the signal processing system 10 detects the state of reaction of the particular material in the sample liquid 15 with the sensing medium 14, and causes the display means 11 to display the result of detection.

Such measurement is made in parallel to the other fifteen sample wells 23 and the sample liquid in the sixteen sample wells 23 are measured at one time. Projection of the light beam and detection of the attenuation angle $\theta$sp need not be done strictly at one time for the sixteen sample wells 23 but may be done at somewhat different times.

As described above, whether there is contained in the sample liquid 15 particular material combined with the sensing medium 14 can be detected by measuring change of the attenuation angle $\theta$sp before and after the sample liquid is dispensed in the sample wells 23. In order to remove influence of the solvent of the sample liquid on the change of the refractive index, the measurement is done with buffer of the same components as the sample liquid stored in the sample well 23.

A certain time is required between measurement before dispensation of the sample liquid (before reaction) and measurement after dispensation of the sample liquid (after reaction) due to dispensation of the sample liquid and a predetermined reaction time. In order to better use the intervals between the measurement before reaction of the sample liquid and the measurement after reaction of the sample liquid, batch processing in which a sensor unit is once demounted from the measuring means after a measurement before reaction, another sensor unit is mounted on the measuring means, and then the measurement before reaction is made on said another sensor unit is generally carried out, thereby increasing the throughput capacity of the apparatus.

On the other hand, since the batch processing requires demounting and remounting the sensor unit, there has been a problem that the position of the interface in the measurement after reaction can be displaced from the position of the interface in the measurement before reaction due to thermal expansion of the sensor unit 20, which can cause a measuring error (an error produced when the state of light reflected in total internal reflection is measured).

In the measuring apparatus of this embodiment, temperature change of the sensor unit 20 after it is conveyed to the measuring system 4 from the constant temperature system 3 is estimated by the CPU 2 on the basis of the temperature difference between the temperature of the constant temperature system 3 (the predetermined temperature) and the measured temperature of the measuring system 4, and the sensor unit 20 is conveyed to the measuring system to perform the measurement within a time for which the temperature of the sensor unit 20 does not change from the predetermined temperature by a temperature range which is larger than an acceptable temperature range, whereby fluctuation in temperature of the sensor unit 20 upon measurement is suppressed and deterioration in measuring accuracy is prevented. Control of the sample analysis by the CPU2 will be described hereinbelow.

Buffer solution is first dispensed by the dispenser 8 in the sample wells 23 of a sensor unit 20 waiting in the exterior. Then the sensor unit 20 is conveyed to the constant temperature system 3 and left to stand there until the temperature of the sensor unit 20 is equalized to the temperature T2 of the constant temperature system 3.

Then the conveyor means 7 is caused to convey the sensor unit 20 to the sensor holding means 18 of the surface plasmon resonance sensor 5 and the measurement before reaction is made on the sample wells 23 of the sensor unit 20 within the acceptable time $T_{limit}$.

After the measurement before reaction, the sample liquid 15 is dispensed to the sample wells 23 thereof by the dispenser 8 and the sensor unit 20 is returned to the constant temperature system 3 by the conveyor means 7.

Thereafter, the conveyor means 7 is again caused to convey the sensor unit 20 to the sensor holding means 18 of the surface plasmon resonance sensor 5 and the measurement after reaction is made on the sample wells 23 of the sensor unit 20 within the acceptable time $T_{limit}$. The time between the dispensation of the sample liquid 15 and the measurement after reaction may be determined according to the sample or the like so long as the temperature of the sensor unit 20 returned to the constant temperature system 3 is equalized to the temperature T2 of the constant temperature system 3.

The with the particular material in the sample liquid 15 to be combined with the sensing medium 14 (if any) combined with the sensing medium 14, and by subtracting the measured value before reaction from the measured value after reaction, net change of the refractive index due to reaction of the analyte can be detected.

In this embodiment, since the measurement after reaction is made with the temperature of the sensor unit 20 held at substantially the same temperature as that in the measurement before reaction, change of the refractive index accurately reflecting the reaction of the analyte can be detected without being affected by the thermal expansion of the sensor unit 20.

As described above, the measurement before or after reaction on one or more sensor unit 20 is done between the measurement before reaction of a certain sensor unit 20 and the measurement after reaction of the certain sensor unit 20.

Not only to detect change of the refractive index between before and after reaction but also to detect change with time of the reaction, measurement is to be done a plurality of times at predetermined intervals. In both the cases, substantially the same temperature of the sensor unit 20 can be reproduced each time the sensor unit 20 is set to the sensor holding means 18. Further, also in quantitative analysis of the analyte based on the attenuation angle, the sensor unit 20 can be held at substantially the same temperature upon measurements before and after reaction and the attenuation angle for the sample can be accurately measured, whereby reliability of the measuring apparatus can be improved.

Figure 10:
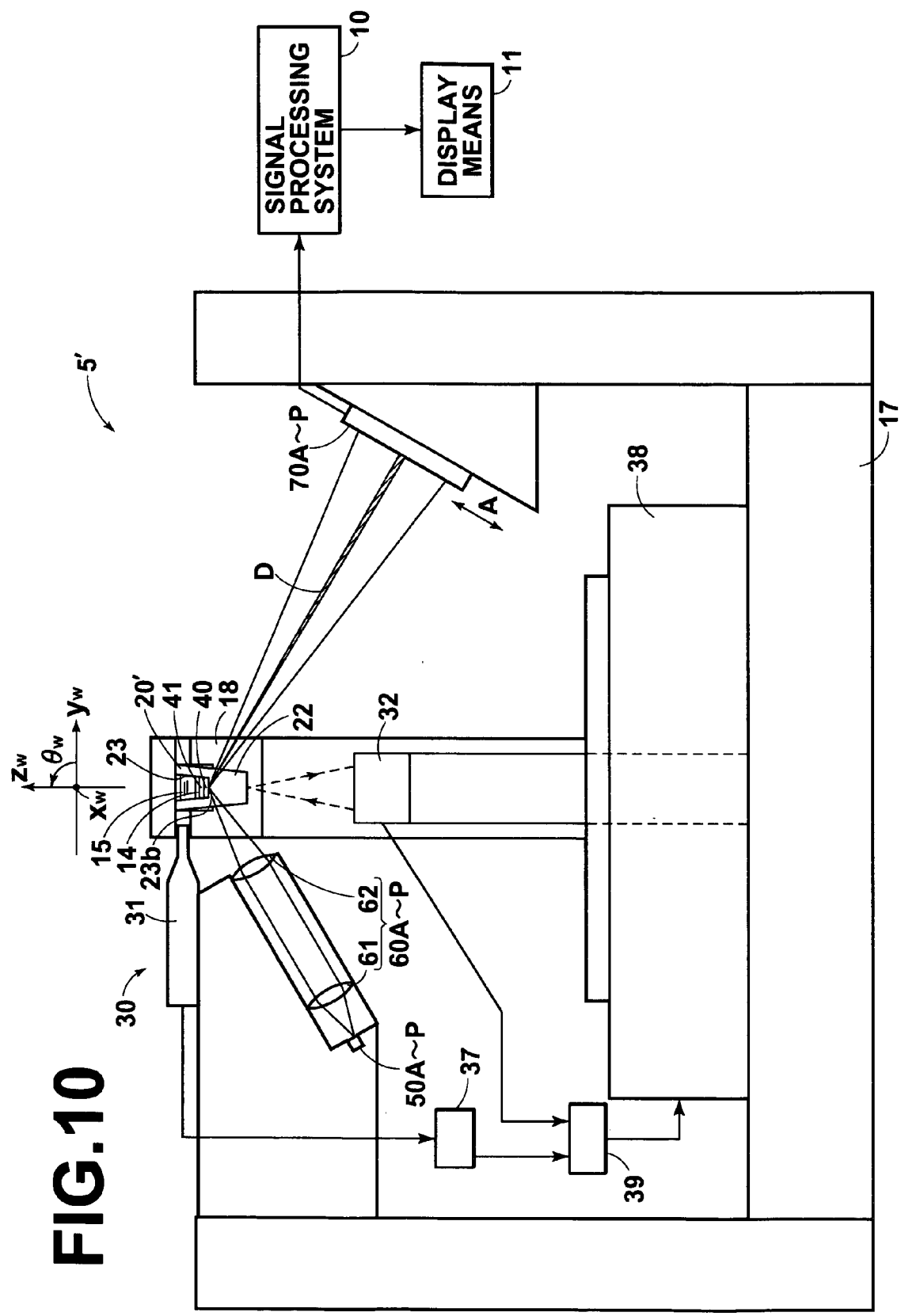
FIG. 10 is a side cross-sectional view of a leaky mode sensor in accordance with a second embodiment of the present invention.

A measuring apparatus in accordance with a second embodiment of the present invention will be described with reference to FIG. 10, hereinbelow. In FIG. 10, the elements analogous to those shown in FIG. 2 are given the same reference numerals and will not be described. Only the difference from the second embodiment will be mainly described hereinbelow.

The measuring means in this embodiment is a leaky mode sensor described above and is provided with a sensor unit 20' having a plurality of sensor wells 23. However, a clad layer 40 is formed on the bottom surface of each sample well 23 in place of the metal film 12 and an optical waveguide layer 41 is formed on the clad layer 40. The arrangement of the other part is identical to the surface plasmon resonance sensor in the first embodiment.

In the leaky mode sensor in this embodiment, the body 21 of the sensor unit 20' is formed of synthetic resin or optical glass (e.g., BK7), and the clad layer 40 is in the form of film of dielectric material or metal (e.g., gold) which is lower in refractive index than the body 21. The optical waveguide layer 41 is in the form of film of dielectric material which is higher in refractive index than the clad layer 40 (e.g., PMMA). For example, the clad layer 40 is 36.5 nm in thickness when it is in the form of a metal film and the optical waveguide layer 41 is 700 nm in thickness when it is formed of PMMA.

In the leaky mode sensor with this arrangement, when the light beam L emitted from the light source 50 is caused to impinge upon the clad layer 40 through the dielectric block 22 at an angle not smaller than an angle of total internal reflection, the light beam L reflected in total reflection at the interface 23b between the dielectric block 22 and the clad layer 40 and the light having a particular wave number and impinging upon the optical waveguide layer 41 at a particular angle of incidence comes to propagate through the optical waveguide layer 41 in a waveguide mode after passing through the clad layer 40. When the waveguide mode is thus excited, almost all the incident light is taken in the optical waveguide layer 41 and accordingly, the intensity of light reflected in total internal reflection at the interface 23b sharply drops. That is, attenuation in total internal reflection occurs.

Since the wave number of light to be propagated through the optical waveguide layer 41 in a waveguide mode depends upon the refractive index of the sample 15 on the optical waveguide layer 41, the refractive index and/or the properties of the sample 15 related to the refractive index can be detected on the basis of the angle of incidence at which the attenuation in total internal reflection occurs. Further, by providing a sensing medium 14, which combines with a particular material on the optical waveguide layer 41, whether the sample liquid 15 includes the particular material can be detected as in the surface plasmon resonance sensor.

Also in this embodiment, effects similar to that in the first embodiment can be obtained.

Figure 11:
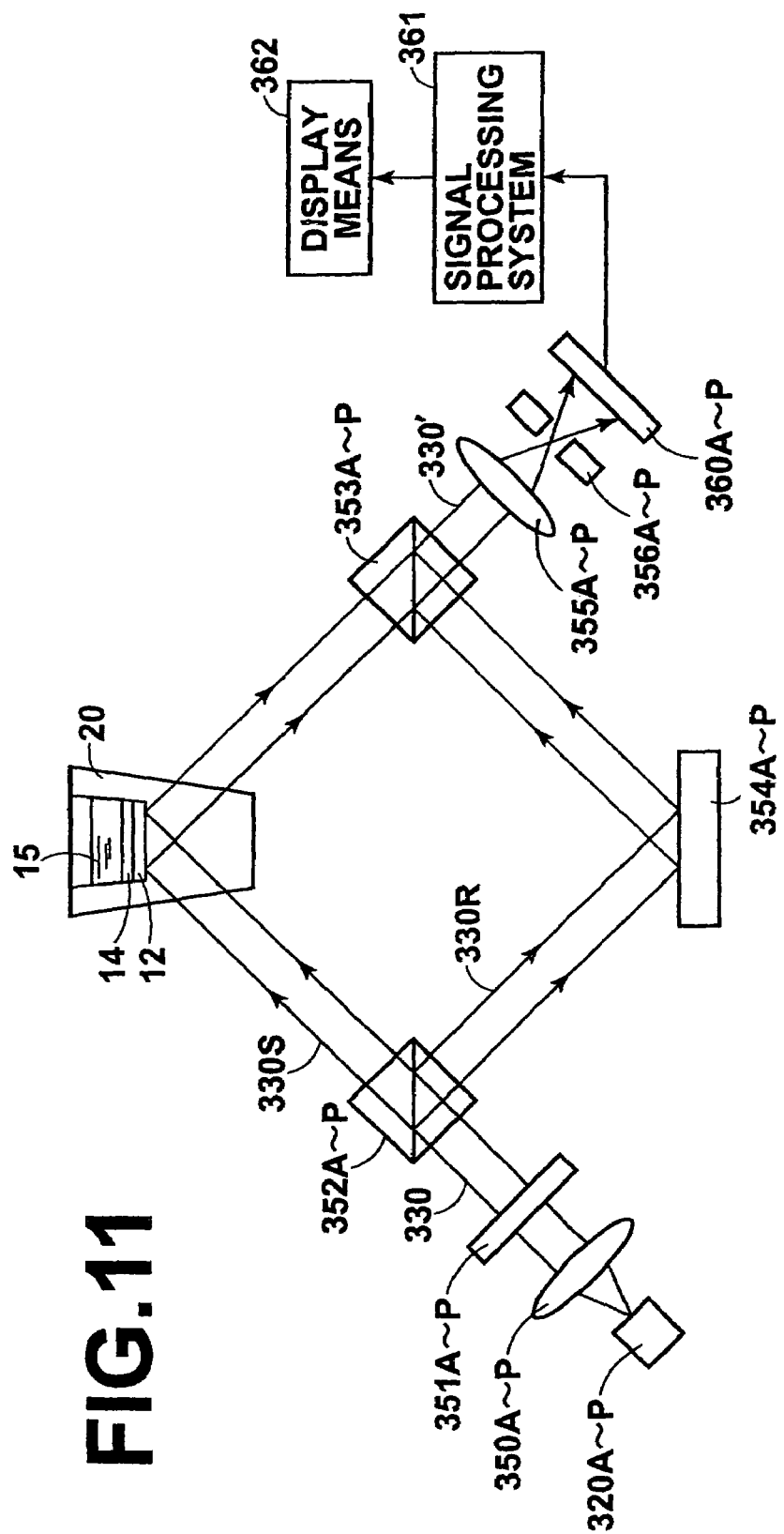
FIG. 11 is a side cross-sectional view of a measuring apparatus in accordance with a third embodiment of the present invention.

A measuring apparatus in accordance with a third embodiment of the present invention will be described with reference to FIG. 11, which is a schematic view showing an important part of the measuring apparatus in accordance with the third embodiment of the present invention, hereinbelow. The measuring apparatus of this embodiment differs from that of the first embodiment only in the measuring means. Only the method of measurement for obtaining the state of combination of the analyte with the sensing medium, which differs from the preceding embodiments, is shown in FIG. 11 and will be described hereinbelow.

In the measuring apparatus of this embodiment. light sources 320A to 320P, and CCDs 360A to 360P are disposed on opposite sides of the sensor unit 20. Collimator lenses 350A to 350P, interference optical systems, condenser lenses 355A to 355P, and apertures 356A to 356P are disposed between the light sources 320A to 320P, and the CCDs 360A to 360P.

The interference optical systems are formed by polarization filters 351A to 351P, half-silvered mirrors 352A to 352P, half-silvered mirrors 353A to 353P and mirrors 354A to 354P.

The CCDs 360A to 360P are connected to a signal processing section 361 and the signal processing section 361 is connected to a display means 362.

Measurement on samples by the measuring apparatus of this embodiment will be described, hereinbelow.

The light sources 320a to 320e are operated and light beams 330A to 330P are emitted therefrom as divergent light beams. The light beams 330A to 330P are collimated respectively by the collimator lenses 350A to 350P and impinge upon the polarization filters 351A to 351E. The light beams 330A to 330P polarized by the polarization filters 351A to 351P to impinge upon the interfaces in a p-polarized state are split into two light beams each by the half-silvered mirrors 352A to 352P. One of the two light beams is reflected by the corresponding one of the half-silvered mirrors 352A to 352P and forms a reference light beam 330R, whereas the other light beam 330S passes through the corresponding one of the half-silvered mirrors 352A to 352P and impinges upon corresponding one of the interfaces. Each of the light beams 330S reflected in total internal reflection at the interface and each of the reference light beams 330R reflected at mirrors 354A to 354P impinge upon corresponding one of the half-silvered mirrors 354A to 354P and synthesized into a light beam 330'. The synthesized light beam 330' is condensed by corresponding one of the condenser lenses 355A to 355P, and impinges upon the corresponding one of the CCDs 360A to 360P through the corresponding one of the apertures 356A to 356P. The light beam 330' detected by the corresponding one of the CCDs 360A to 360P generates interference fringes according to the state of interference of the light beam 330S and the reference light beam 330R.

By continuously measuring a plurality of times after the sample 15 is dispensed to detect the change of the interference fringes, bonding of the particular material with the sensing medium 14 can be detected. That is, since the refractive index of the sensing medium 14 changes with the state of bonding of the particular material with the sensing medium 14 and the state of the interference fringes generated by interference of the light beam 330S reflected in total internal reflection at the interface and the reference light beam 330R synthesized by corresponding one of the half-silvered mirrors 353A to 353P changes with the refractive index of the sensing medium 14, bonding of the particular material with the sensing medium 14 can be detected by detecting the change of the interference fringes.

The signal processing section 361 detects existence of the reaction on the basis of the above principle, and the display means 362 displays the result of the detection.

Also in this embodiment, effects similar to that in the first embodiment can be obtained.

Though, in the embodiments described above, the sensor unit is provided with a plurality of one-dimensionally arranged sample wells, a senor well unit having only one sample well (the conventional sample tip) or a plurality of two-dimensionally arranged sample wells may be employed.

Figure 12:
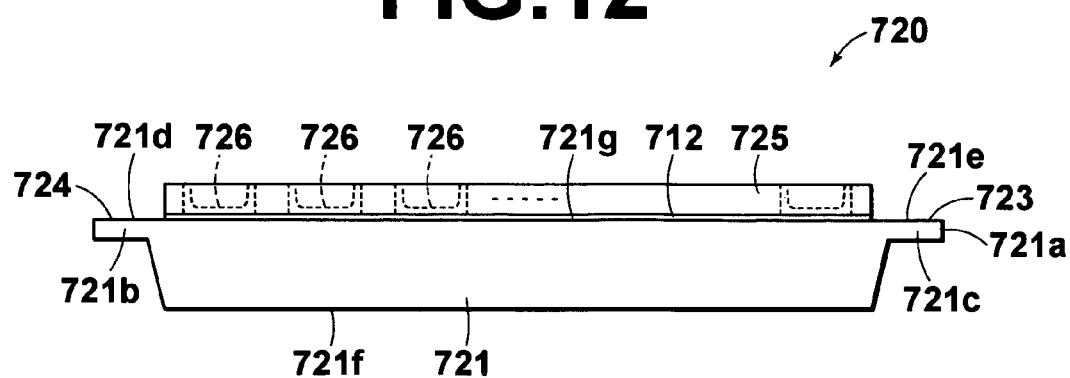
FIG. 12 is a front view showing a sensor unit having a flow passage member.
Figure 13:
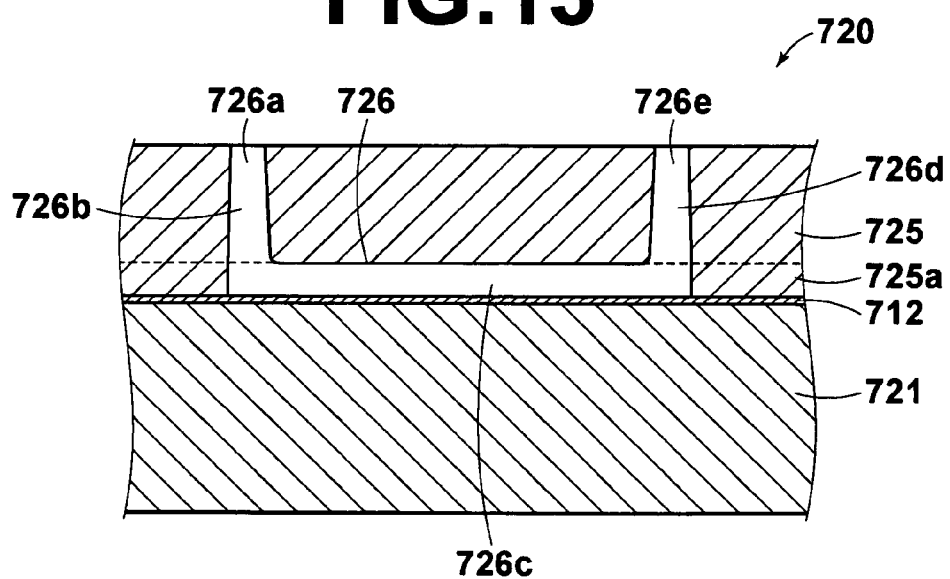
FIG. 13 is a fragmentary cross-sectional view of the sensor unit shown in FIG. 12.

As other sensor units, those having a flow passage member which will be described hereinbelow can be used. A sensor unit having such a flow passage member will be described, hereinbelow. FIG. 12 is a front view showing a sensor unit having a flow passage member, and FIG. 13 is a fragmentary cross-sectional view of the sensor unit.

The sensor unit 720 comprises a dielectric body (unit body) 721 transparent to the light beam, a thin metal film 712 formed on the smooth upper surface 721g of the dielectric body 721, and a flow passage member 725 in close contact with the metal film 712. The outer bottom surface 721f of the body 721 is taken as the reference surface for position measurement.

First and second flanges 723 and 724 which are the same in thickness project outward respectively from the left and right ends of the body 721. The flanges 723 and 724 have flat upper surfaces 721d and 721e flush with the upper surface 721g of the body 721.

The flow passage member 725 is provided with a plurality of flow passages 726 linearly arranged in the longitudinal direction of the flow passage member 725. Each of the flow passages 726 comprises a supply passage 726b extending from an inlet port 726a to a measuring portion 726c, and a discharge passage 726d extending from the measuring portion 726c to an outlet port 726e.

As shown in FIG. 13, the outlet of the supply passage 726b and the inlet of the discharge passage 726d open in the lower portion of the flow passage member 725, and a sealing portion 725a is formed to surround the outlet of the supply passage 726b and the inlet of the discharge passage 726d in the region in contact with the metal film 712. The inside of the sealing portion 725a forms the measuring portion 726c, and accordingly, when the flow passage member 725 is brought into close contact with the metal film 712 on the dielectric block 721, the measuring portion 726c in the sealing portion 725a functions as a flow passage. That is, the flow passage member 725 functions as the sample holding portion. The sealing portion 725a may be either integrally formed with the upper portion of the flow passage member 725 or formed of a material different from the upper portion of the flow passage member 725 and attached by post handling. For example, an O-ring may be mounted on the lower portion of the flow passage member 725.

A sample liquid containing protein is expected to be used in the sensor unit 720. If the protein in the sample liquid is solidified in the flow passages 726, it becomes difficult to accurately effect the measurement. Accordingly, it is preferred that the material of the flow passage member 725 has not non-specific adsorptivity to protein and the flow passage member 725 is preferably formed of silicone or polypropylene.

When a sample liquid is to be supplied to the sensor unit 720, a pipette chip for sample supply is inserted into the inlet port 726*a* of the flow passage member 725, while a pipette chip for sample suction is inserted into the outlet port 726*e*, and the sample liquid is supplied to the measuring portion 726*c* through the pipette chip for sample supply.

The sensor unit 720 can be applied to any one of the first to third embodiments described above.

What is claimed is:

1. A measuring apparatus comprising
   a sensor unit comprising a dielectric block, a thin film layer which is formed on the upper surface of the dielectric block, and a sample holding portion which holds a sample on the thin film layers
   a light source emitting a light beam,
   a sensor holding means which demountably holds the sensor unit in a predetermined position,
   a light beam projecting means which causes the light beam to enter the dielectric block to impinge upon the interface between the upper surface of the dielectric block and the thin film layer so that total internal reflection conditions are satisfied at the interface,
   a measuring means provided with a refractive index information obtaining means which obtains refractive index information on analyte on the thin film layer on the basis of the light beam reflected at the interface,
   a measuring system which accommodates the measuring means,
   a temperature measuring means which measures the temperature of the measuring system,
   a constant temperature system which is controlled to be at a predetermined temperature and stores the sensor unit,
   a conveyor means which selectively positions the sensor unit in a predetermined position in the measuring system or in the constant temperature system, and
   a controlling means which controls the measuring means and the conveyor means, wherein the improvement comprises that
   the controlling means estimates temperature change of the sensor unit after it is conveyed to the measuring system from the constant temperature system on the basis of the temperature difference between the predetermined temperature and the measured temperature of the measuring system as measured by the temperature measuring means, and drives the conveyor means to convey the sensor unit to the measuring system and the measuring means to perform the measurement within a time for which the temperature of the sensor unit does not change from the predetermined temperature by a temperature range which is larger than an acceptable temperature range.

2. A measuring apparatus comprising
   a sensor unit comprising a dielectric block, a thin film layer which is formed on the upper surface of the dielectric block, and a sample holding portion which holds a sample on the thin film layer
   a light source emitting a light beam,
   a sensor holding means which demountably holds the sensor unit in a predetermined position,
   a light beam projecting means which causes the light beam to enter the dielectric block to impinge upon the interface between the upper surface of the dielectric block and the thin film layer so that total internal reflection conditions are satisfied at the interface,
   a measuring means provided with a refractive index information obtaining means which obtains refractive index information on analyte on the thin film layer on the basis of the light beam reflected at the interface,
   a measuring system which accommodates the measuring means,
   a temperature measuring means which measures the temperature of the measuring system,
   a constant temperature system which is controlled to be at a predetermined temperature and stores the sensor unit,
   a conveyor means which selectively positions the sensor unit in a predetermined position in the measuring system or in the constant temperature system, and
   a controlling means which controls the measuring means and
   the conveyor means, wherein the improvement comprises that the controlling means estimates temperature change of the sensor unit after it is conveyed to the measuring system from the constant temperature system on the basis of the temperature difference between the predetermined temperature and the measured temperature of the measuring system as measured by the temperature measuring means, and drives the conveyor means to convey the sensor unit to the measuring system and the measuring means to perform the measurement in a time range for which the temperature of the sensor unit is kept in a particular temperature range.

* * * * *